United States Patent
Ingimundarson et al.

(10) Patent No.: US 7,077,818 B2
(45) Date of Patent: * Jul. 18, 2006

(54) ANKLE-FOOT ORTHOSIS

(75) Inventors: Arni Thor Ingimundarson, Reykjavik (IS); Orn Olafsson, Hafnarfjordur (IS); Arinbjorn Viggo Clausen, Reykjavik (IS); Kim Peter Viviane De Roy, Reykjavik (IS)

(73) Assignee: OSSUR hf, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 11/167,087

(22) Filed: Jun. 28, 2005

(65) Prior Publication Data

US 2005/0234378 A1    Oct. 20, 2005

Related U.S. Application Data

(63) Continuation of application No. 10/702,447, filed on Nov. 7, 2003, now Pat. No. 6,945,947.

(60) Provisional application No. 60/424,321, filed on Nov. 7, 2002.

(51) Int. Cl.
*A61F 5/00* (2006.01)
*A61F 5/37* (2006.01)

(52) U.S. Cl. .............. 602/27; 602/28; 602/29; 602/65; 128/882

(58) Field of Classification Search ........... 602/27–30, 602/23, 60–62, 65–66; 128/869, 882; 623/27–29, 623/47; 2/22
See application file for complete search history.

(56) References Cited

U.S. PATENT DOCUMENTS

| | | | |
|---|---|---|---|
| 2,949,111 | A | 8/1960 | Ruotoistenmaki |
| 4,538,599 | A | 9/1985 | Lindemann |
| 4,646,726 | A | 3/1987 | Westin et al. |
| 4,922,895 | A | 5/1990 | Chong |
| 5,038,762 | A | 8/1991 | Hess et al. |
| 5,219,324 | A | 6/1993 | Hall |
| 5,520,628 | A | 5/1996 | Wehr |
| 5,609,568 | A | 3/1997 | Andrews |
| 5,776,090 | A | 7/1998 | Bergmann et al. |
| 5,817,041 | A | 10/1998 | Bader |
| 5,897,515 | A | 4/1999 | Willner et al. |
| 5,961,477 | A | 10/1999 | Turtzo |
| 6,146,344 | A | 11/2000 | Bader |
| 6,146,349 | A | 11/2000 | Rothschild et al. |
| 6,334,854 | B1 | 1/2002 | Davis |
| 6,428,493 | B1 | 8/2002 | Pior et al. |

(Continued)

FOREIGN PATENT DOCUMENTS

DE    197 22 118 A1    2/1999

(Continued)

OTHER PUBLICATIONS

Clinician's Corner, "Basic Anatomic Terms", downloaded on Feb. 25, 2005, http://www.footmaxx.com/clinicians/anatomic.html, pp. 1-5.

*Primary Examiner*—Henry Bennett
*Assistant Examiner*—Shumaya B. Ali
(74) *Attorney, Agent, or Firm*—Bacon & Thomas PLLC

(57) ABSTRACT

An ankle-foot orthosis having a structural frame formed from at least one layer of fabric impregnated with a hardened structural resin. The frame includes at least one anterior support member that extends downwardly from an upper leg engaging portion to define an anterior ankle portion which extends to a medial portion connected to a foot plate.

18 Claims, 6 Drawing Sheets

U.S. PATENT DOCUMENTS

| | | |
|---|---|---|
| 6,676,618 B1 | 1/2004 | Andersen |
| 6,692,454 B1 | 2/2004 | Townsend et al. |
| 6,726,645 B1 | 4/2004 | Davis |
| 6,887,213 B1 | 5/2005 | Smits |
| 2001/0031935 A1 | 10/2001 | Andersen |
| 2001/0051780 A1 | 12/2001 | Birmingham |
| 2002/0029009 A1* | 3/2002 | Bowman ............... 602/27 |
| 2003/0125653 A1 | 7/2003 | Meyer |
| 2003/0153862 A1 | 8/2003 | Watts |

FOREIGN PATENT DOCUMENTS

| | | |
|---|---|---|
| WO | 01/34071 A1 | 5/2001 |
| WO | 02/083040 A1 | 10/2002 |
| WO | 03/002042 A1 | 1/2003 |

\* cited by examiner

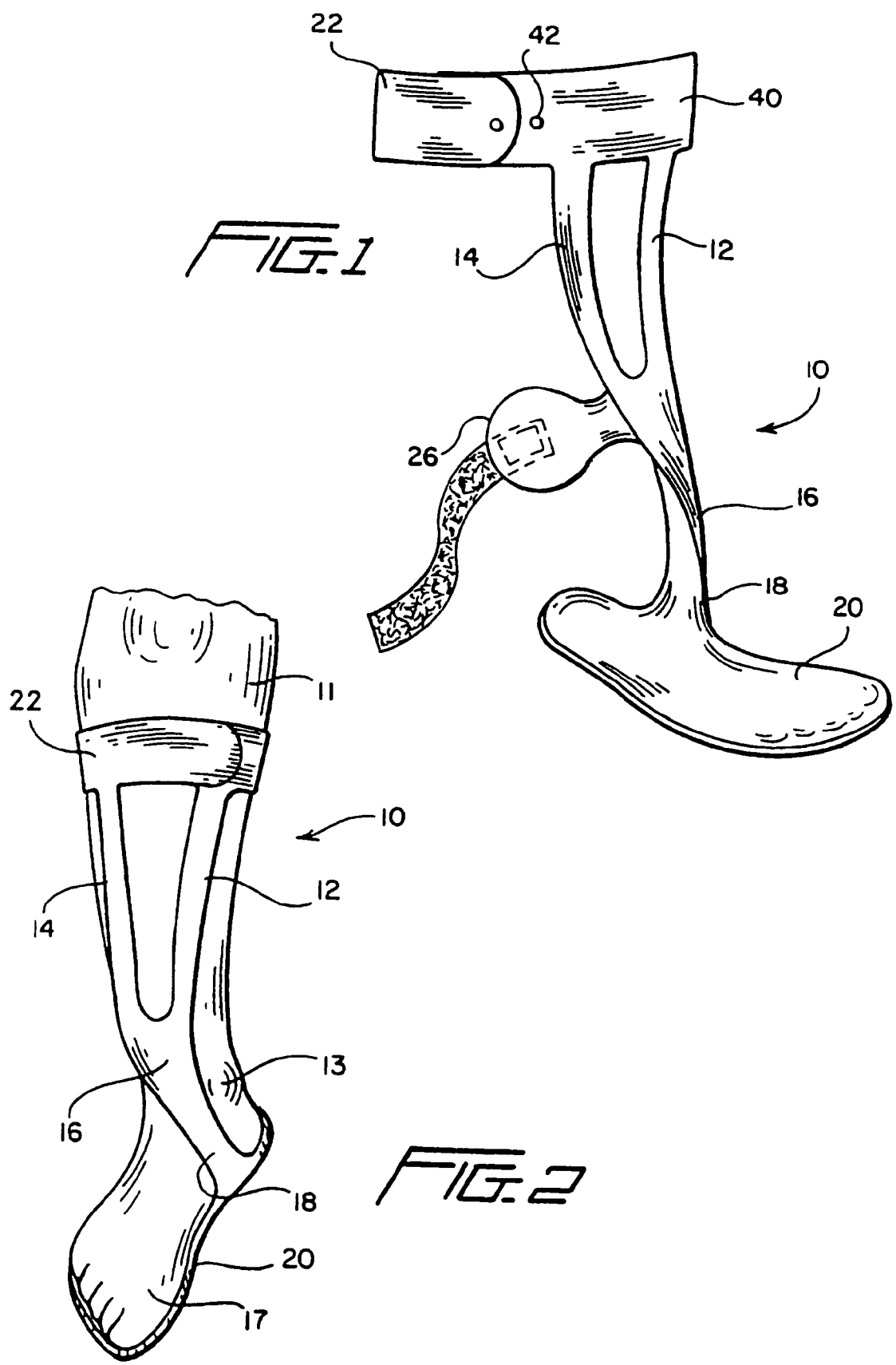

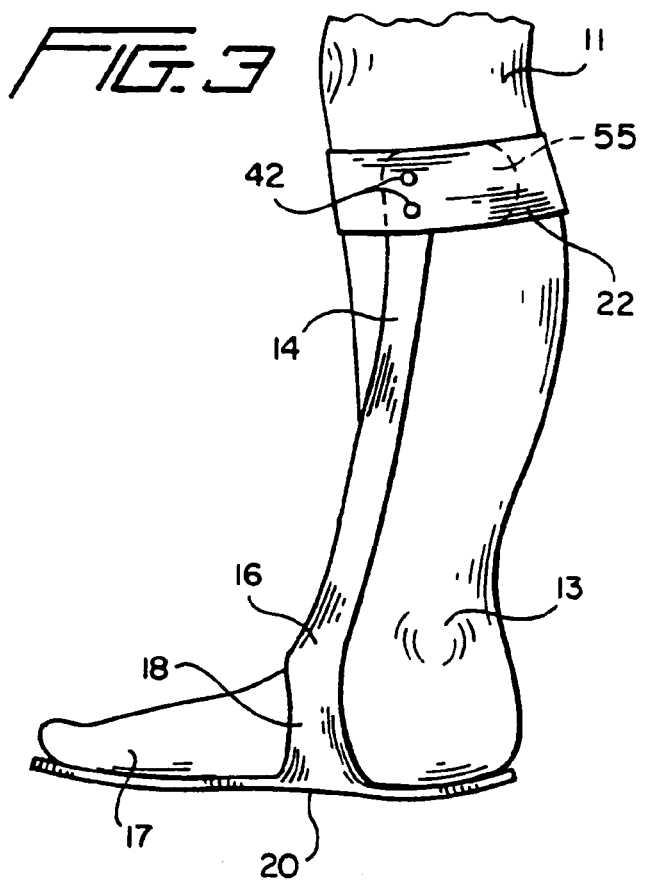
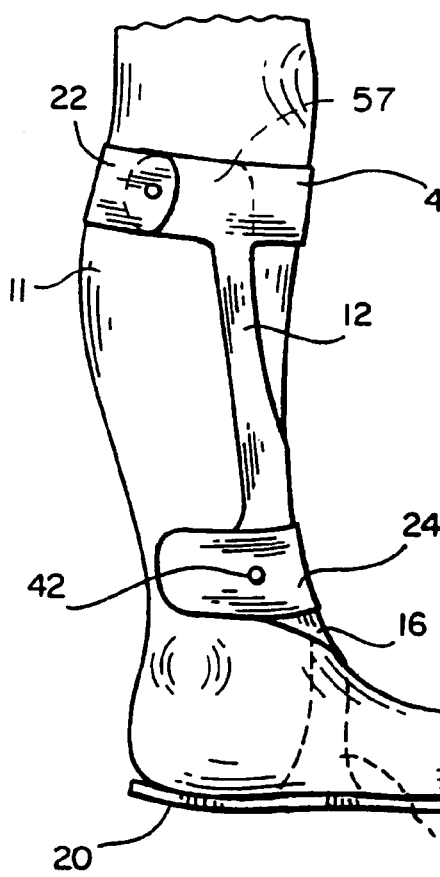

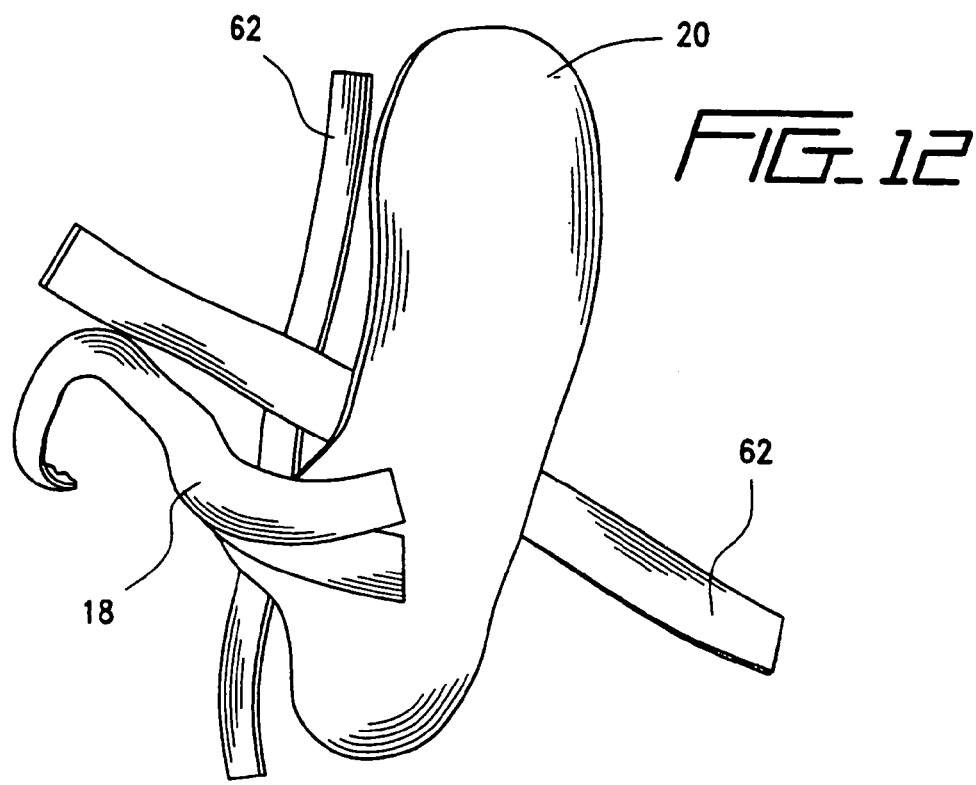
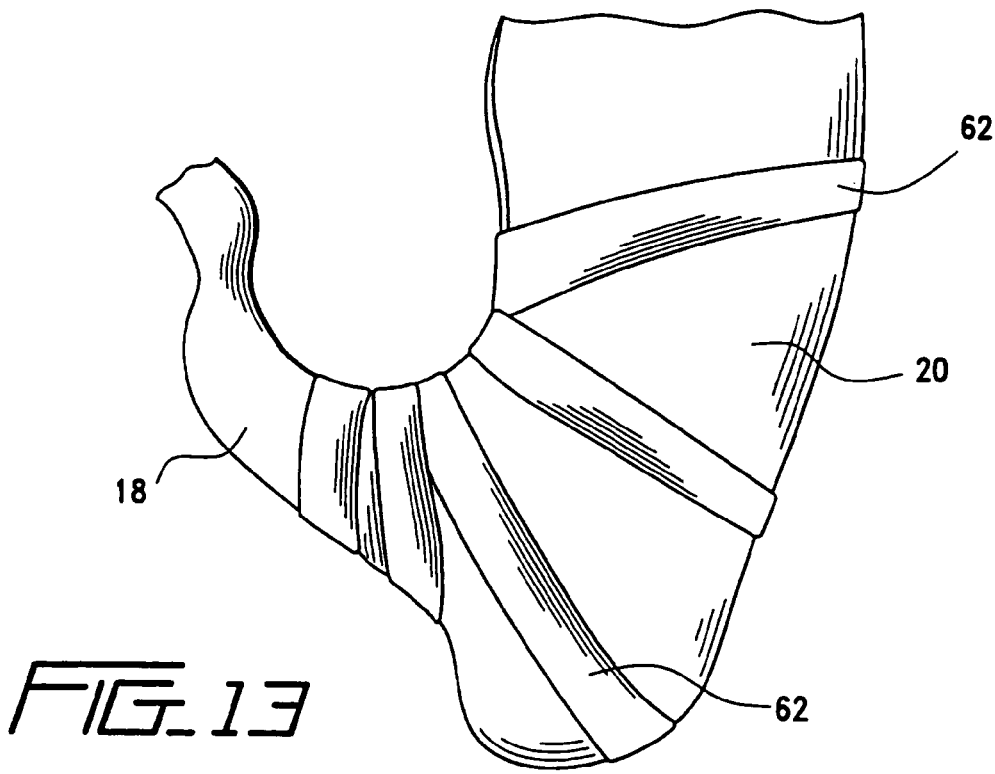

ANKLE-FOOT ORTHOSIS

This application is continuation application of application Ser. No. 10/702,447 filed Nov. 7, 2003, now U.S. Pat No. 6,945,947, which claims the benefit of U.S. provisional ppplication No. 60/424,321, filed Nov. 07, 2002.

BACKGROUND

1. Field of the Invention

The present invention relates to orthotic devices utilized to limit the movement of a lower limb. More particularly, the present invention relates to an ankle-foot orthosis for stabilizing and controlling motion of the ankle and foot.

2. Description of the Related Art

An ankle-foot orthosis is a medical device used to support and align the ankle and foot by suppressing spastic and overpowering ankle and foot muscles, assisting weak and paralyzed muscles of the ankle and foot, and preventing or correcting ankle and foot deformities.

An ankle-foot orthosis is particularly useful in assisting the functions of the ankle and foot when a person has a gait condition commonly known as "drop foot." Drop foot is a neuro-muscular condition resulting in the inability of a person to sufficiently lift one of their feet during a walking stride. Drop foot may result from a cerebrovascular accident, spinal cord injury, hereditary and sensory neuropathies, neuromuscular disease or any damage to the muscle and nerves required to activate the muscle of the neuromuscular system related to the foot.

There are two common complications from drop foot. First, the individual cannot control the falling of their foot after striking their heel. Consequently, the foot will slap the ground on every step, which is commonly referred to as slap foot. This is typically due to the impairment of a patient's dorsiflexor muscles which are located below the knee on the front of the leg and used to lift the foot from a position substantially aligned with the lower leg to a position substantially perpendicular to the lower leg known as dorsiflexion. Impairment of the dorsiflexor muscles thus results in excessive plantar flexion which is the action of extending the foot from a position substantially perpendicular to the lower leg to a position substantially parallel to the lower leg. The second complication is the inability to clear the toe during the swing phase of a gait cycle. This causes the person to drag their toe on the ground throughout the swing phase. Hence, an ankle-foot orthosis can be prescribed to compensate for the weakness of the dorsiflexors by resisting plantar flexion at the heel strike and swing phase during a gait cycle.

Typically, an individual with drop foot may have little or no function in their anterior tibialis. The anterior tibialis originates at the lateral condyle of the tibia and extends along the lateral side of the tibia to cross the tibia near a distal portion thereof over to the medial side of the ankle to connect with the first metatarsal bone and medial cuneiform bone. Proper function of the anterior tibialis permits dorsiflexion and inverts the foot at the ankle in a supinated position. The anterior tibialis also supports the medial arch of the foot due to its connection to the medial cuneiform bone.

Individuals who have lost function of the anterior tibialis tend to pronate during a stance phase of a gait cycle, and supinate the foot during a swing phase of a gait cycle. Furthermore, due to impairment of the anterior tibialis, in particular at the medial arch of the foot, the ankle is typically everted and pronated.

Over the years, efforts have been made to provide ankle-foot orthotic devices to correct drop foot and enable a patient to walk and function in a relatively normal manner. One type of prior art ankle-foot orthosis comprises a dorsal splint of metal or plastic that extends behind the Achilles tendon and merges with a foot plate spanning the sole of the foot. This ankle-foot orthosis has at least one strap which extends around the lower leg at a location below the knee. This ankle-foot orthosis is disadvantageous in that the orthosis extends along the dorsal portion of the leg and affects the joints unfavorably to produce a very stiff gait. Another disadvantage to this orthosis is that the calf and Achilles tendon are subjected to heavy stresses which may cause pain and discomfort to the patient wearing the orthosis. Yet further, this orthosis has an undesirable effect on a patient's leg during a gait cycle since the orthosis is solely positioned on the back of the heel and therefore does not provide a smooth heel strike.

Another type of prior art ankle-foot orthosis is produced by Otto Bock and sold under the trade name "Walk On." This ankle-foot orthosis is fabricated from carbon fiber reinforced material to provide moderate resistance to plantarflexion and dorsiflexion as well as some coronal plane control. The construction of this orthosis includes a footplate connecting to a calf band via a small carbon fiber spring that extends around the medial malleolus and extends up the posterior calf region, and further includes a strap that secures the orthosis to the lower leg. The foot plate provides compression at heel strike, energy return from a mid-stance to toe off, easy toe rollover by including increased stiffness from heel strike to midstance and decreased stiffness from midstance. This design is less conspicuous when worn, since it extends around the medial malleoulus and the carbon fiber reinforced material is wear resistant. Furthermore, this design has the advantage over conventional plastic posterior designs in that it extends over the medial side of the foot, and therefore provides the orthosis with a heel part and a toe part that contribute to a smoother heelstrike. Contrariwise, a disadvantage to this orthosis is that it permits a significant degree of plantar flexion since it lacks proper anterior support and only reinforces the posterior of the ankle and foot. Moreover, this design does not provide any lateral support, and therefore, unless people wear high and strong shoes, inversion of the foot is not prevented.

In another variation of an ankle-foot orthosis, U.S. Pat. No. 5,897,515 discloses an ankle-foot orthosis that includes a frame of flexible material that extends over the anterior portion of the lower leg and the lateral ankle, and further extends beneath a portion of the sole of the foot to connect to a foot plate. This orthosis requires at least one substantially inflexible reinforcement element extending over a narrow part of the anterior portion of the frame. In practice, it has been found that the anterior shell covering the lower leg can cause a patient discomfort due to the amount of area covered along the anterior portion of the leg, thereby resulting in an excessively sweaty area and an undesirable amount of pressure exerted on the tibia region when walking. Furthermore, this orthosis has been found to suffer from breakage problems particularly in a region where the orthosis extends over the lateral ankle and connects to the foot plate.

In an orthosis that includes a strut that extends over a lateral portion of the tibia, as in the orthosis of U.S. Pat. No. 5,897,515, a patient may have adequate support during the swing phase of their gait, but will not have sufficient support to prevent eversion of the foot during the stance phase of their gait. The lack of support during the stance phase is due in part to the lack of support to the medial arch of the foot and the overall failure of the lateral strut to support the length of the anterior tibialis. While many conventional ankle-foot orthoses with a laterally extending strut may provide a patient with more control for dorsiflexion and inhibit excessive plantar flexion, it has thus been found that these orthoses fail to provide adequate support to the medial arch of the foot. As a result, patients that wear these conventional orthoses do not have sufficient force to keep their foot from pronating since their ability to invert the foot has not been increased. Moreover, orthoses with only lateral struts do not provide sufficient valgus control, thereby insufficiently stabilizing an ankle and failing to enable adequate ankle articulation.

With all of the aforementioned orthoses, each fail in part to adequately provide sufficient medial support during a stance phase of a patient's gait and sufficient lateral support during a swing phase of a patient's gait.

Accordingly, it is readily apparent that there is a need for an ankle-foot orthosis that provides support for both the medial and lateral ankle portions of a patient, dynamic dorsiflexion and plantar flexion support, a foot plate permitting easy toe rollover, and a dynamic design which is more durable and less prone to material failure through normal use.

SUMMARY

It is a primary object of the present invention to overcome the aforementioned shortcomings associated with the prior art.

Another object of the present invention is to provide an ankle-foot orthosis that provides dynamic plantar flexion support to provide a more natural and dynamic gait while maintaining the foot in a functional position.

Yet another object of the present invention is to provide an ankle-foot orthosis having a monolithic frame for supporting the anterior portion of the lower leg which does not cover the entire anterior portion of the lower leg while maintaining a light, strong and durable orthosis.

A further object of the present invention is to provide an ankle-foot orthosis that provides a smooth toe rollover or transition of compressive forces from a heel-strike position to a toe-off position so as to provide a natural feeling when walking while wearing the orthosis.

These as well as additional objects of the present invention are achieved by providing an ankle-foot orthosis preferably having a structural frame including at least one layer of fabric impregnated with a hardened structural resin. In one embodiment of the present invention, the frame is monolithic and includes two anterior support members configured and dimensioned to extend downwardly from below the knee of a patient over the anterior a patient's leg to define a clearance therebetween along the length thereof. The anterior support members join in advance of an ankle joint of a patient to define an anterior ankle portion which extends to a medial portion or strut extending around the medial ankle of a patient and connecting to a foot plate beneath the sole of a foot of a patient.

The foot plate may have a curvilinear shape and variable stiffness properties between the heel and toe ends. The design of the foot plate in the present invention provides a smooth toe rollover or transition of compressive forces from a heel-strike position to a toe-off position thereby providing a natural feeling during a walking stride while a patient wears the orthosis. In areas of the orthosis that are subject to higher degrees of stress relative to other areas, such areas are reinforced with additional reinforcing fibers.

Unlike the aforementioned orthotic devices of the prior art, the orthosis of the present invention includes a medial strut or portion arranged to extend generally along the tibialis anterior and over the medial ankle. With medial support provided for the ankle, the orthosis provides a three-point pressure system wherein two pressure points are located on the lateral side of the shoe and the lateral side of an upper calf of the patient. The third pressure point extends along the medial strut and prevents the foot from pronating and the ankle from assuming a fixed structural position in which the foot or part of the foot appears everted or in the valgus position.

Further advantages of the invention will become apparent to those skilled in the art from the following detailed description and drawings referenced therein.

BRIEF DESCRIPTION OF THE DRAWINGS

FIG. 1 is a perspective view of one embodiment of the orthosis of the present invention;

FIG. 2 is a perspective view of one embodiment of the orthosis of the present invention on a lower right leg of a patient;

FIG. 3 is a side view of another embodiment of the orthosis on a lower right leg of a patient;

FIG. 4 is another side view of the orthosis on a lower right leg of a patient;

FIGS. 12 and 13 are schematic views showing the formation of reinforcement regions of the orthosis of the present invention.

DETAILED DESCRIPTION OF VARIOUS EMBODIMENTS

Figure 5:
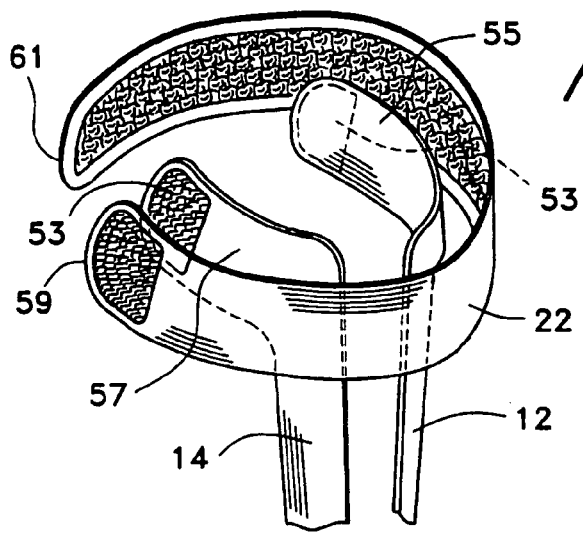
FIG. 5 is a perspective view of the orthosis having a preferred strap device.

With reference to FIGS. 1 and 2, a preferred embodiment of the ankle-foot orthosis of the present invention is shown. The ankle-foot orthosis generally comprises a monolithic frame 10 including at least one layer of fabric impregnated with a hardened structural resin. In this embodiment, the orthosis includes lateral and medial anterior support members 12, 14, respectively, configured and dimensioned to extend downwardly from below a knee of a patient's leg 11 along the anterior of the leg 11 thereby defining a clearance therebetween along a portion of the length of the leg 11. The lateral and medial anterior support members 12, 14 join in advance of a patient's ankle joint 13 to define an anterior ankle portion 16. The ankle portion 16 preferably extends to a medial connection 18 extending around the medial side of a patient's ankle 13 and connecting to a foot plate 20 located beneath the sole of a patient's foot 17.

Alternatively, the ankle portion may extend to a lateral connection that extends around the lateral side of a patient's ankle and connects to the foot plate, or the ankle portion may extend to a combination of lateral and medial connections that extend around respective portions of a patient's ankle and connect to a foot plate.

The configuration of the two anterior support members 12, 14 permits easy adjustment around the leg and a preferred fit is achieved by adjusting the two anterior support members 12, 14 relative to one another according to the preference of the patient. The configuration of the frame 10 may also permit some forward bend of the leg 11 which provides spring to the region of the frame 10 at an upper portion of the lower leg 11 and relieves some pressure of the orthosis on the leg 11 and ankle 13 near the footplate 20. In addition, the configuration of the frame 10 enables ample air circulation around the face of the lower leg.

The two anterior support members 12, 14 preferably remain bifurcated generally two-thirds the distance from their proximal end to the foot plate 20. It has been found that there is an increase in rigidity and decrease in flexibility of the frame if the anterior support members are lengthened resulting in a shortened ankle portion, and conversely, a decrease in rigidity and increase in flexibility if the anterior support members are shortened resulting in an elongated ankle portion. It will be understood that it is within the scope of the present invention to lengthen or shorten the anterior support members from the preferred two-thirds distance length in order to gain greater rigidity or flexibility.

While in a preferred embodiment the anterior support members 12, 14 may have the same rigidity, the anterior support members may be constructed so that each member has a different stiffness. For example, the lateral anterior member may be more rigid than the medial anterior member, or vice versa. In addition, one of the anterior support members may be longer than the other anterior support member, or similarly, one of the anterior support members may have a greater width or thickness than the other anterior support member. The length, width or thickness of the anterior support members may be optimized to accommodate particular needs of a patient.

Although the frame of the orthosis of the present invention has been described as having two anterior support members the frame may alternatively consist of a single anterior support member or more than two anterior support members as may be necessary depending upon a patient's conditions.

The ankle-foot orthosis of the present invention may be arranged in at least several different configurations to connect the frame to the leg of a patient. In the embodiment shown in FIG. 1, the lateral and medial anterior support members 12, 14 are connected by a lateral frame element 40 extending laterally across the leg 11. Connected to lateral and medial sides of the lateral frame element 40 is a fastening device 22 configured to wrap around the leg 11 to secure the frame 10 thereon. The lateral frame element 40 includes fastener elements 42 arranged to permit the fastening device 22 to be releasably secured therewith. Although buttons and button holes, snap fasteners, or other similar fasteners commonly used may be employed, much preferred are complementary sections of hook-and-loop fastener fabric mounted on opposite overlapping sides of the lateral frame element 40 and the fastening device 22.

The lateral frame element may be integrated with the frame when the frame is formed, or may alternatively be permanently or releasably secured to the frame after the frame has been formed. The lateral frame element may be constructed from structural materials such as resin impregnated glass, carbon or aramid fibers, a polymer such as polyethylene or polyurethane, or any other material suitable for an ankle-foot orthosis known to one skilled in the art. Additionally, the lateral frame element may comprise a textile and padding combination, whether combined with a structural material or taken alone, that is sufficiently rigid to provide support to the patient.

In another embodiment shown in FIGS. 2, 3 and 4, the fastening device 22 connects to the lateral and medial anterior support members 12, 14 and wraps around the leg 11 to secure the frame therewith. As shown in FIGS. 3, 4, the frame 10 of this embodiment includes upper leg engaging portions 55, 57 that extend from and generally are oriented perpendicularly relative to the anterior support members 12, 14. Such upper leg engaging portions 55, 57 are configured to extend around at least a portion of the periphery of the patent's leg 11, thereby providing lateral support to the leg and sufficient surface area to secure the frame 10 to such leg 11.

The fastener device may be constructed from a textile, elastic band or any other material that may be apparent to one skilled in the art for wrapping around the leg and securing the lateral and medial anterior support members thereon. Moreover, the fastener device may be formed from at least one material having breathable properties which may reduce a build-up of localized areas of sweat on the leg or a material that can store and release energy to withhold desirable temperature to thereby reduce localized regions of sweat.

As illustrated in FIG. 5, hook-and-loop segments 53 of a hook-and-loop material are preferably secured to the anterior support members 12, 14 on the upper engaging portions 55, 57 thereof. The fastening device 22 is preferably secured at a fixed end 59 to one of the upper engaging portions 55 and includes a portion of hook-and-loop material complementary to the hook-and-loop segments 53. A free end 61 of the fastening device 22 is configured and dimensioned to extend around a patient's leg to couple with the hook-and-loop segments 53. An advantage to this particular embodiment is that it permits easy adjustment of the fastener strap 44 and firmly secures the frame 10 to a patient's leg by preventing movement of the anterior support members 12, 14 in relation to the leg.

In this particular embodiment, it is preferred that the hook-and-loop segments 53 are adhered to the anterior support members as the frame 10 is formed. For example, during manufacturing of the frame, a polymeric coated textile may be pulled over fiber laminates used to form the frame and cured with the fiber laminates in an autoclave. A small incision is made on the textile at a region of the upper engaging portions of the anterior support members where the fastening device will be attached. The hook-and-loop segments are glued over the incisions on the textile so that during curing of the resin of the laminate, the resin will leak through the cuts and into the hook-and-loop segment, thereby forming a bond with the hook-and-loop segments.

While this particular embodiment is advantageous in that it is more visually appealing, it also simplifies the attachment of the orthosis on a patient's leg. The hook-and-loop segments in combination with the fastening device allow the free end of the strap to be removably attached to the patient's leg in a variety of positions and with the possibility of incremental adjustment.

Figure 6:
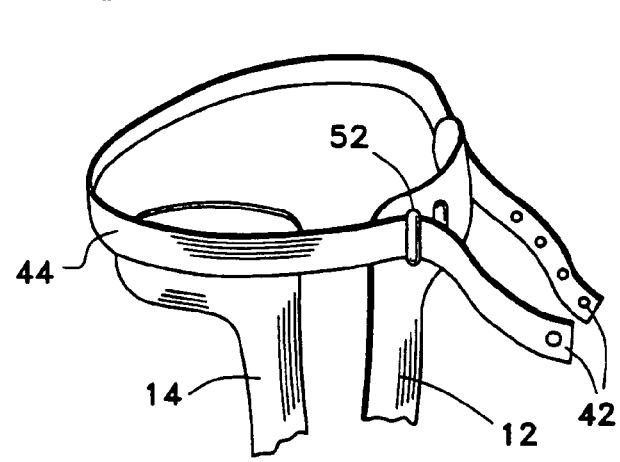
FIG. 6 is a perspective view of the orthosis having another preferred strap device.

In yet another embodiment shown in FIG. 6, the frame 10 includes a fastener strap 44 configured and dimensioned to wrap around an upper calf region of a patient and extend through at least one loop 52 connected to either one or both of the lateral and medial anterior support members 12, 14. Both ends of the fastener strap 44 may include fastener elements 42, such as those mentioned above, which are configured to couple with a corresponding one on an opposite strap end of the fastener strap 44. The fastener strap 44 may be fixed onto at least one of the anterior support members 12, 14, or may be an unattached, loose strap that is insertable through the at least one loop 52.

The orthosis of the present invention may include support members that are used to reinforce the frame. Such additional reinforcement members may be releasably secured to the frame or integrated therewith to selectively provide additional support to regions of the leg.

As shown in FIG. 1, the frame 10 may be provided with a lateral leg support 26 that extends generally from a location near a proximal portion of the ankle portion 16 and wraps around the calf region of a patient. The lateral leg support 26 may be releasably connected to the frame 10 or integrated therewith and include additional layers of preimpregnated fabric, bendable layers of molded glass fibers or reformable prepeg material attached to either interior or exterior portions of the frame 10. In the event the frame 10 is formed with the lateral leg support 26 and it is found that the support is not necessary, the lateral leg support may be removed from frame in a manner known to one skilled in the art of orthotics.

Alternatively, as shown in FIG. 4, the invention may include a lateral ankle support 24 that is located near a distal portion of the ankle portion 16 and extends laterally thereon. The lateral ankle support 24 may be integrated with the frame or may be releasably secured to the frame with fastener elements 42, such as those mentioned above. The lateral ankle support can be employed to extend over the patient's foot 17 to provide additional support to prevent supination during the swing phase of a gait cycle, a condition of which is common with drop foot patients.

The ankle-foot orthosis of the present invention may be configured in a variety of embodiments that are aimed to provide comfort to the patient wearing such an orthosis.

In one embodiment of the invention, at least one of the anterior support members may include a padding feature disposed on the surface which faces the patient's leg. This padding feature may be coated onto localized surfaces of the frame, integrated within the frame at predetermined areas, or may extend in a continuous web between the anterior support members to span the clearance therebetween. Such padding feature is preferably soft and lightweight, provides excellent shock absorption and prevents blistering of the skin. Preferred materials used in the padding feature include a flexible foam made from cross-linked, closed cell foam, or silicone layer made from incompressible silicone. Moreover, it is preferred that the padding feature include a textile cover disposed over the aforementioned materials.

In another embodiment, the interior of the anterior support members may include a portion of hook-and-loop material adhered to the surface thereof. Padding material having a corresponding portion of hook-and-loop material may be provided so that a patient can selectively remove or install the padding material to the anterior support members. In another embodiment, the padding material may be prefabricated to provide an exact fit to the orthosis, generally having the same profile as the portions of the frame. The configuration of the padding material is not limited to being disposed only along the interior surface of the anterior support members, but may also extend over the exterior surface of the anterior support members or around the entire periphery of the orthosis to thereby form a sleeve-like structure.

In another embodiment of the orthosis, a web may be provided to span the clearance between the anterior support members to effectively create a shell over the anterior portion of the leg. This web is preferably flexible so as not to impede the function of the anterior support members but sufficiently rigid to provide additional support to the leg. The flexible web may be a laminate material, woven glass fibers, neoprene, elastic cotton, rubber, foam rubber, latex, silicone, any other suitable flexible material known to one skilled in the art and any combination thereof. Alternatively, the web may not be flexible and may be selected from the group consisting of cotton, canvas, vinyl, nylon, any other suitable flexible material known to one skilled in the art and any combination thereof. The web may be sewn, woven, fastened, glued or secured to the frame in any other fashion known to one skilled in the art.

The frame is preferably constructed of a plurality of layers of woven glass fibers reinforced with a plastic resin. The woven glass fibers may be reinforced with resin impregnated carbon or aramid fibers in a plastic resin at specific locations of the frame, thereby providing additional structural strength and varying degrees of flexibility. In one embodiment of the invention, the frame is reinforced with unidirectional carbon fibers along the anterior support members the anterior ankle portion, the medial connection and the foot plate. In this embodiment, it is preferred that the unidirectional carbon fibers are generally oriented along the longitudinal length of the frame. In addition, it is also preferred in this embodiment that the woven glass fibers are generally oriented at 45 degrees relative to the unidirectional carbon fibers so as to provide optimal strength and flexibility. It is also preferred that the medial connection and the foot plate be reinforced with a plurality of aramid fibers preimpregnated with an epoxy matrix to provide additional toughness and flexibility required for durability.

Portions of the frame may exclusively be constructed from woven glass fibers and the orientation of such fibers may be provided in a predetermined manner. For example, it is preferred that the upper engaging portions 55, 57 in FIG. 5 extending from the anterior support members be solely constructed from woven glass fibers wherein the glass fibers are preferably oriented at 45 degrees and multiples thereof relative to the width thereof extending around a patient's leg 17. Furthermore, the same orientation of glass fibers used in the upper engaging portions may be provided for the lateral leg support 26 in FIG. 1.

It will be understood that specific regions of the frame may include additional layers of fibers reinforced with a plastic resin to provide greater structural strength at such regions. For example, the medial portion of the frame may have a greater thickness than the anterior support members so as to provide a more rigid connection between the foot plate and the ankle portion and to withstand the forces subjected thereto when a patient walks.

In other arrangements, the frame and the foot plate may include other materials, such as fiber glass, silicone, polyurethane coated lycra, polyurethane film, Alkantara and plastic covered textile as will be apparent to one skilled in the art. Desirable material properties of the frame and the foot plate should possess sufficient resiliency to resist cracking upon application of repeated bending stresses, and ample flexibility to enhance performance characteristics felt by a patient to provide a more natural and dynamic gait while a patient's foot is in a functional position.

It will be understood that the present invention is not limited to the aforementioned types, location and orientation of fibers, and may be tailored to include or omit certain fibers construction at various locations according to a desired flexibility and strength. Furthermore, the frame and foot plate of the present invention may be constructed from a polymer, such as polyethylene or polyurethane, and may selectively be reinforced with at least one structural material or composite.

Selected regions of the orthosis of the present invention may be coated with a polymeric coated textile, such as a polyurethane coated lycra or neoprene, to provide a smooth surface finish and prevent localized areas of delamination of the fibers. Preferably, the selected regions include the surfaces of the anterior support members, ankle anterior portion, the medial portion not in contact with the patient's leg and all of the external surfaces of the foot plate. It will be understood, however, that the coating is not limited to being disposed on the described selected regions and may be provided on any of the surfaces of the frame.

Preferably, the coating of the orthosis is performed by stretching a polymeric coated textile over the frame after a laminate fiber lay-up and before the frame is placed in an autoclave. When the resin of the laminate begins to cure, the fibers cure with the polyurethane coated lycra as well. This provides the orthosis with a visually appealing surface and prevents splinters from the fibers in the event the orthosis delaminates.

Figure 7B:
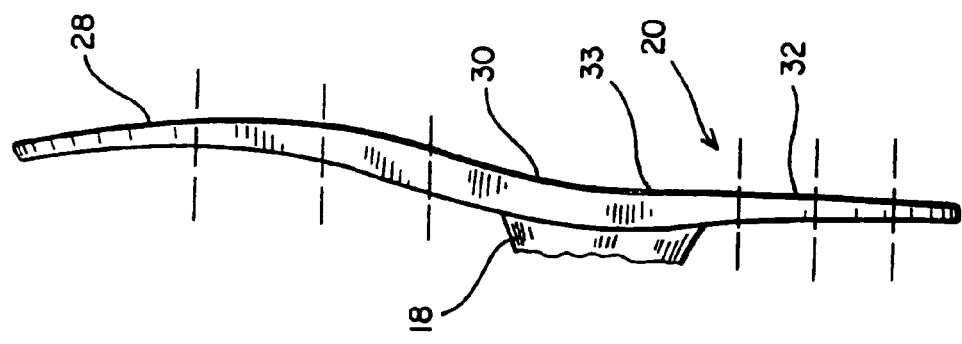
FIG. 7B is a side elevational view of the foot plate of FIG. 7A.
Figure 7A:
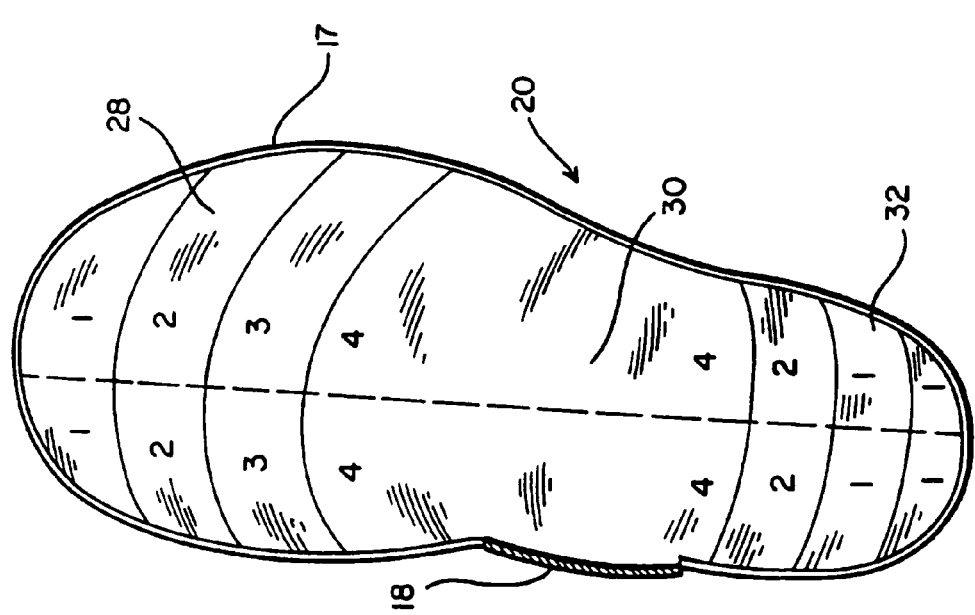
FIG. 7A is a top plan view of one embodiment of the foot plate of the present invention showing varying regions having different relative thicknesses.

Turning to the foot plate 20, FIGS. 7A and 7B show the foot plate 20 preferably having a length from toe to heel roughly equal to the sole of the foot 17. The foot plate 20 includes a toe end 28, a heel end 32 and an intermediate region 30 therebetween. The foot plate 20 substantially conforms to the foot 17 and defines a curvilinear shape having a tapered thickness that generally decreases from the intermediate region 30 to the heel end 32 and toe ends 28.

The performance of the foot plate 20 is concerned with four positions of the foot 17 during a walking stride. The first position of a walking stride entails a heel strike, wherein the patient transfers weight to the heel of the leading foot. The flexible nature of the foot plate 20 allows the heel end 32 to bend slightly in the rear portion thereof although most compressive stresses from the weight of the patient are absorbed by the ankle which is reinforced by the medial connection 18. As shown in FIG. 7A, the relative thickness of the heel end 32, as evidenced by the numerals, is greater at regions approaching the intermediate portion 30.

The second position occurs during midstance or when the patient reaches a generally flat foot-footed position when the foot plate 20 contacts the ground substantially along its entire length. The compression weight of the patient in this position is continually shifting from the heel end to the toe end in a movement which is called "rollover." As shown in FIG. 7A, the intermediate region 30 maintains a constant thickness along the length thereof to provide a uniform rollover effect.

FIG. 7B shows an alternative embodiment of the invention wherein the heel end 32 of the foot plate 20 bends downward 33 relative to the intermediate region 30. The downward bend 33 provides additional spring and dampening to the heel end 32 during the rollover and heel-off positions. The downward bend 33 delays emergence of the foot condition "flat foot," a condition which occurs when a patient cannot achieve the rigidity of a normal foot and a common early symptom of drop foot. As an alternative to delay the emergence of flat foot, the foot plate 20 may alternatively be provided with a variable stiffness as opposed to providing a bend in foot plate 20.

The third position occurs when the patient pushes off the ball and toe regions of the foot at a terminal stance at the "heel-off" position. As a result, the toe end 28 is subject to large compressive forces and may bend substantially with the foot of the patient to absorb some of the compressive stresses. As can be seen in FIGS. 7A and 7B, the relative thickness decreases from the intermediate region 30 to the toe end 28. In the heel-off position the ankle portion absorbs a majority of the compression generated by the patient, and the foot plate 20 and the ankle portion 16 work to provide dynamic performance.

In the fourth position, some of the weight of the patient is being transferred to the opposite foot. In this position there is less bending of the toe end 28 and the ankle portion 16 flex a slight amount. This position is termed as the "toe off" position.

The desirable thicknesses of the aforementioned regions of the foot plate 20 may be tailored according to a patient's condition as may be apparent to one skilled in the art. Therefore, the foot plate 20 of the present invention as shown in FIGS. 7A and 7B is not limited to the relative different thicknesses shown therein.

Although the foot plate should cover substantially the length of the foot to provide sufficient control to a patient's gait while distributing pressure from the foot, the foot plate may be positioned offset from a medial side of the foot so as to generally cover a central portion of the sole of the foot. By offsetting the foot plate, pressure can be relieved from an anterior portion of the leg and the ankle. Furthermore, medial portions of the foot plate may be removed to achieve the offset position thereof relative to a medial side of the foot. In addition, portions of the toe end and the heel end may be removed to assist in providing a more custom fit of the foot plate in a shoe and to relieve pressure on portions of the orthosis.

The foot plate of the invention may have a widened lateral portion relative to a medial portion thereof so that the lateral portion of the foot plate presses more against a patient's shoe on the lateral side than on the medial side. The widened lateral portion of foot plate is provided so that the medial portion of the orthosis does not aggravate the navicular bone of a patient's foot.

The foot plate 20 includes unidirectional fiber plies that are layered in combination with woven fiber plies along the length thereof. The amount of unidirectional fiber plies and the woven fiber plies provided along different areas 28, 30 and 32 vary in accordance with the different thickness discussed in relation to FIGS. 7A and 7B.

Figure 8:
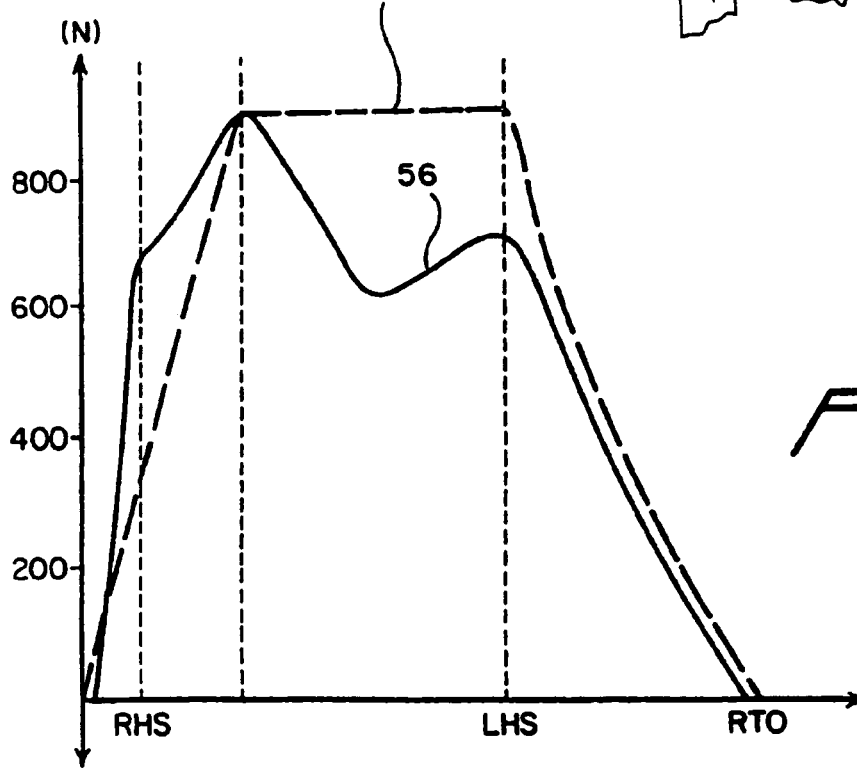
FIG. 8 is a graph showing the relationship between foot plate stiffness and forces exerted by a person having a normal walking gait.

FIG. 8 shows a force analysis of a healthy person walking to demonstrate how stiffness of a right-footed foot plate of the present invention varies during a right heel strike (RHS), left heel strike (LHS) and right toe off (RTO). The solid line 56 represents forces that a person having a normal gait applies to a floor when walking. The dashed line 54 represents the stiffness of the foot plate from the heel 32 to the toe 28 ends. By example, assuming that the foot plate is 10 inches, RHS represents a point taken 1.5 inches from the heel end 32 and LHS represents a point taken 7.5 inches from the heel end 32. It follows that RTO represents a point taken 10 inches from the heel end 32.

Figure 9:
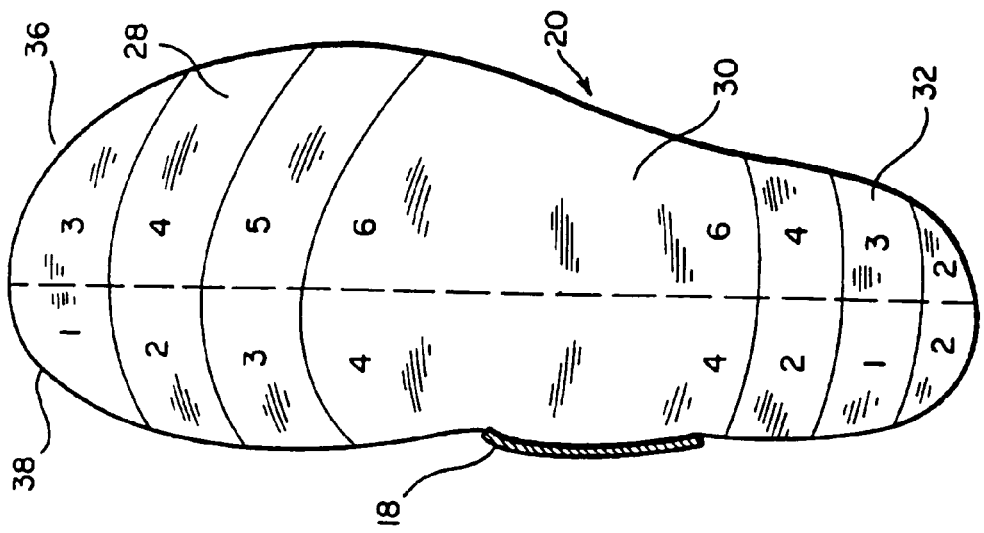
FIG. 9 is a schematic view of the foot plate of the present invention showing a comparison between the amount of fiber layers and unidirectional fiber layers of the foot plate.

FIG. 9 shows a schematic view illustrating the number of unidirectional fiber plies relative to the woven fiber plies of the foot plate 20. On the medial side 38 of the foot plate 20, FIG. 9 shows a predetermined number of unidirectional plies of fibers positioned along the regions 28, 30 and 32. On the lateral side 36 of the foot plate 20, FIG. 9 shows the combined total of unidirectional fiber plies and woven plies of fibers positioned along regions 28, 30 and 32 of the foot plate 20.

Figure 10:
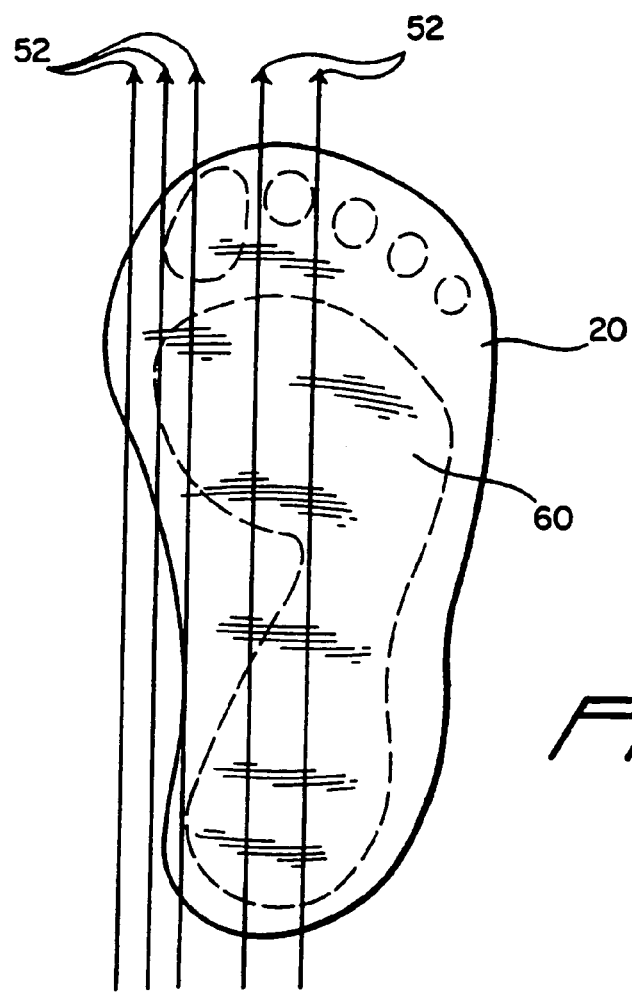
FIG. 10 is a schematic view showing the direction of the unidirectional fibers positioned along the foot plate.

FIG. 10 schematically shows the direction 52 of the unidirectional fibers along the length of the foot plate 20 in relation to the imprint 60 of a patient's foot. The fibers are positioned generally in direction 52 which is in the direction of the reaction force movement between the ground and the foot, and tension that builds in the foot plate 20 when a patient is walking. By positioning the unidirectional fibers in the direction of the reaction force, rotational movement of the foot is minimized when a patient is walking while wearing the orthosis.

Figure 11:
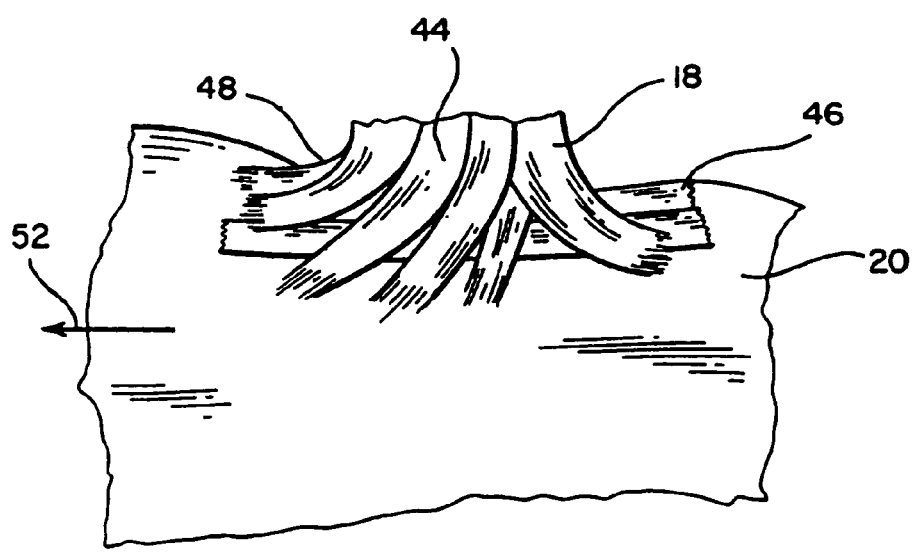
FIG. 11 is a schematic view showing the fibers extending from the medial connection to the foot plate.

As shown in FIG. 11, the unidirectional fibers 46 of the foot plate 20 are arranged unidirectionally along the length of the foot plate 20 such that layers of fibers 44 extending from the medial connection 18 interleave with the fibers 46 of the foot plate 20. The unidirectional fibers 44 change direction when they reach the foot plate 20 and extend in direction 52. The interface between the medial connection fibers 44 and the unidirectional fibers 46 is provided to strengthen the orthosis between the medial connection 18 and the foot plate 20 and to reduce the risk of material failure of the orthosis 20 at point 48 between the medial connection 18 and the foot plate 20 which is a prevalent area of orthosis fracture.

By changing the number of layers of the medial connection to the footplate in combination with changing the number of layers in the footplate itself, one can alter the stiffness of the orthosis to better suit each patient. The proper stiffness is crucial to control the rate of plantar flexion right after heel strike to prevent foot slap. As mentioned above, patients who have drop foot have partial or total impairment of the foot dorsiflexors which results in the patient slapping his feet at heel strike and striking his toes onto ground during the swing phase of a gait cycle. The dorsiflexor moment required at these two stages of gait is significantly different since the moment required to hold the foot up during swing is only the weight of the foot multiplied by the short leverage arm from the center of mass in the foot to the rotation arm of the ankle. On the other hand, the moment required during the plantar flexion right at heel strike is significantly higher since weight plays a factor since the patient shifts his body weight onto the foot when he puts his heel to the ground.

The fibers 44 extending from the medial portion 18 are laid along the foot plate 20 in separate layers to prevent voids in the foot plate 20 and to decrease stresses on the foot plate 20 during a walking stride. It should be noted that by placing all the layers from the medial portion in between the same two layers of the footplate, very high stresses on just one area in the footplate may result. Consequently, there may be a greater number of voids since all the layers extending from the medial portion are bulky, and it follows that it would be difficult to remove the voids between layers. It has been found that by placing just 2–4 layers of fibers from the medial portion to the footplate, then placing one layer of the footplate over such layers, and repeating this sequence until the lay-up is finished, one can greatly decrease the presence of voids and increase the area of pressure for the fibers from the medial portion with the footplate layers.

During fabrication, a vacuum is applied to the connection between the foot plate 20 and the medial portion 18 in at least one stage in order to reduce air in the lamination of the fiber layers 44, 46. It is important to the present invention that the voids are removed or kept at a minimum since it has been found that durability of the orthosis markedly decreases with a rise in voids between the layers of fibers.

Aramid fibers may be integrated with the fiber layers 46 of the foot plate 20 to increase the flexibility and toughness thereof, and to reduce the risk of material failure. Aramid fibers are also useful in assisting the prevention of delamination of the fiber layers 44 in the event that the foot plate 20 would shatter. While it is envisioned that aramid fibers may be used in a lower portion of the medial connection 18 connecting to the foot plate 20, aramid fibers may be integrated throughout the orthosis wherever one skilled in the art may deem necessary to increase flexibility and toughness thereof.

Preferably, aramid fibers may be integrated in the connection between the medial portion 18 and the footplate 20 where unidirectional aramid fibers turn from the medial portion 18 to the footplate 20. When the cycle of a gait of a patient reaches heel strike, the forces applied to the orthosis are concentrated on the inside of the footplate. Accordingly, it is preferable to reinforce the inside portion of the foot plate with aramid fibers to prevent failure of the orthosis.

In another embodiment of the frame of the present invention, the fibers may be positioned in a three-dimensional fiber lay-up configuration at preselected portions of the frame. As opposed to simply laying the fibers in one direction, a plurality of fibers may be provided and positioned in a different orientation than the unidirectional fibers to create a three-dimensional configuration. It has been found that through cyclic loading, microcracks in the resin of the unidirectional fibers are produced which propagate over time to cause delamination of the layers of unidirectional fibers. By using the three-dimensional approach to laying-up the fibers, delamination of the layers of unidirectional fibers is mitigated since the plurality of fibers oriented in a different direction than the unidirectional fibers bind the unidirectional fibers together.

In one preferred method, the three-dimensional fiber lay-up configuration includes interposing the unidirectional fiber layers with fibers extending at an angle non-parallel to the direction of the unidirectional fibers. For example, while the unidirectional fiber layers may generally extend along a first plane, a plurality of fibers generally extending along a second plane may be interposed with the unidirectional fibers extending along the first plane. Additionally, in the connection between the medial connection and the footplate, the layers of fibers extending from the medial connection to the foot plate may be considered to extend in directions along the first plane in orientations non-parallel to the unidirectional fibers of the foot plate. A plurality of fibers extending in the second plane may be interposed through both the layers of the fibers extending from the medial connection and the foot plate. While the interposed fibers can extend at any angle non-parallel with the unidirectional fibers, it is preferred that the fibers extend perpendicularly to the unidirectional fibers for optimal strength of the configuration.

As shown in FIGS. 12 and 13, another method for forming the three-dimensional fiber configuration may be adopted wherein at least reinforcement member 62 including at least one layer of a plurality of fibers may be provided to reinforce areas of the medial portion 18 and foot plate 20 susceptible to failure. The reinforcement members 62 may be positioned to extend around and over portions of the foot plate 20 at angles non-parallel to the unidirectional fibers of the foot plate and the medial connection. After the initial lay-up of the laminated layers is complete, reinforcement members 62 are wrapped or positioned around the orthosis at areas where delamination may occur.

In this particular three-dimensional configuration, at least a portion of the reinforcement members 62 will include fibers that extend generally along a plane perpendicular to the plane of the unidirectional fibers of the foot plate 20. This will occur at least along areas whereat the reinforcement members wrap around the periphery of the medial connection 18 and foot plate 20. Additionally, in areas where portions of the reinforcement members 62 extend generally along the plane of the unidirectional fibers of the foot plate 20 and medial portion 18, such portions of the reinforcement members 62 provide additional reinforcement to the laminated layers of such foot plate 20 and medial portion 18.

It will be understood that the invention is not limited to the medial portion and the foot plate having reinforced areas with the three-dimensional fiber configuration, and one skilled in the art may provide the orthosis with reinforced regions having the aforesaid three-dimensional fiber connection where deemed necessary.

The orthosis of the present invention can be arranged to be directly casted onto a leg and foot of a patient to form a custom fitted orthosis. Although the orthosis of the present invention permits custom fitting and adjusting over a wide range of dimensional variables, it is preferred to provide the present invention in a range of sizes to permit an orthotist to tailor individualized fitting of the devices to a wide range of individuals within different size and profile ranges.

Alternatively, the orthosis of the present invention can be assembled among a variety of different foot plates, anterior support member, medial portion and ankle portion having various configurations, stiffnesses and sizes. Furthermore, the foot plate and medial portion can be custom shaped to a patient's leg and foot, and the remaining components can be preformed and connected to the custom shaped foot plate and medial portion to form the orthosis of the present invention.

It will be understood that the above described embodiments of the invention are illustrative in nature, and that modifications thereof may occur to those skilled in the art. Accordingly, this invention is not to be regarded as limited to the embodiments disclosed herein, but is to be limited only as defined in the appended claims.

The invention claimed is:

1. An ankle-foot orthosis having medial and lateral sides comprising:
    a structural frame formed from at least one layer of fabric impregnated with a hardened structural resin and including at least one anterior support member extending downwardly from an upper leg engaging portion to an anterior ankle portion, the anterior ankle portion extending to a medial portion located solely on the medial side of the orthosis; and
    the medial portion is contoured to conform to the medial portion of the ankle.

2. The ankle-foot orthosis according to claim 1, further comprising a fastening device connected to the at least one anterior support member at the upper leg engaging portion.

3. The ankle-foot orthosis according to claim 1, further comprising a lateral leg support connected to the frame.

4. The ankle-foot orthosis according to claim 3, wherein the lateral leg support includes a strap arranged to form a loop.

5. The ankle-foot orthosis according to claim 1, wherein the at least one anterior support member, the ankle portion and the medial portion include layers of woven glass fibers reinforced with a plastic resin.

6. The ankle-foot orthosis according to claim 5, wherein at least one portion of the frame includes unidirectionally oriented carbon fibers reinforcing said layers of woven glass fibers.

7. The ankle-foot orthosis according to claim 1, further comprising a layer of polymeric coated textile coating at least a portion of a surface of the structural frame.

8. The ankle-foot orthosis according to claim 1, comprising two anterior support members, the anterior support members defining a clearance therebetween and joining at the anterior ankle portion.

9. The ankle-foot orthosis according to claim 8, wherein the two anterior support members join at the anterior ankle portion at about two-thirds the overall length of the structural frame from the upper leg engaging portion, said overall length of the structural frame defined as the distance from the upper leg engaging portion to a distal end of the medial portion.

10. The ankle-foot orthosis according to claim 9, wherein an upper leg engaging portion extends from the proximal end of each anterior support member, each upper leg engaging portion having a width greater than a width of the anterior support members and a curvilinear profile.

11. The ankle-foot orthosis according to claim 1, wherein the structural frame includes at least one reinforcement integrated into the frame near or at the medial portion, said reinforcement member comprising at least one layer of structural material or composite.

12. The ankle-foot orthosis according to claim 11, wherein the at least one reinforcement member extends over at least a portion of the periphery of a portion of the structural frame.

13. The ankle-foot orthosis according to claim 1, wherein the medial portion has a greater rigidity than the at least one anterior support member and the anterior ankle portion.

14. The ankle-foot orthosis according to claim 1, further comprising a lateral ankle support connected to the anterior ankle portion and extending towards the lateral side of the orthosis.

15. The ankle-foot orthosis according to claim 14, wherein the lateral ankle support is removably detachable from the anterior ankle portion.

16. The ankle-foot orthosis according to claim 14, wherein the lateral ankle support extends from the lateral side of the orthosis to an anterior side of the orthosis.

17. A monolithic ankle-foot orthosis having lateral and medial sides, and a plurality of continuous portions, comprising:
    at least one anterior support portion;
    at least one side portion including a medial portion contoured to conform to the medial portion of the ankle and positioned solely on the medial side of the orthosis; and
    an anterior ankle portion having a proximal end continuously connected to the at least one anterior support member and a distal end continuously connected to the at least one side portion.

18. An ankle-foot orthosis for a human leg, comprising:
    a structural frame including at least one anterior support member extending downwardly from an upper leg engaging portion to an anterior ankle portion, the anterior ankle portion extending to a medial portion contoured to conform to the medial portion of the ankle and located solely on a medial side of the orthosis;
    wherein the anterior ankle portion and the medial portion are positioned to extend over a region of a human leg generally corresponding to the tibialis anterior.

* * * * *